(12) United States Patent
Hector

(10) Patent No.: US 12,193,958 B1
(45) Date of Patent: Jan. 14, 2025

(54) HIP RELOCATION APPARATUS

(71) Applicant: Melvin G. Hector, Tucson, AZ (US)

(72) Inventor: Melvin G. Hector, Tucson, AZ (US)

( * ) Notice: Subject to any disclaimer, the term of this patent is extended or adjusted under 35 U.S.C. 154(b) by 0 days.

(21) Appl. No.: 18/656,072

(22) Filed: May 6, 2024

(51) Int. Cl.
*A61F 5/01* (2006.01)

(52) U.S. Cl.
CPC .................................. *A61F 5/0193* (2013.01)

(58) Field of Classification Search
CPC .... A61F 5/0102; A61F 5/0123; A61F 5/0193; A61F 5/0585; A61G 13/0081; A61G 13/1245; A61G 13/1295; A61G 13/12; A61G 13/123; A61G 13/0036; A61G 2200/327; A61G 2203/42; A61G 2200/325; A61G 7/109; A61G 7/1057; A61B 17/66; A61B 17/1764

See application file for complete search history.

(56) References Cited

U.S. PATENT DOCUMENTS

2005/0160533 A1 * 7/2005 Boucher ................ A61G 13/12
5/624

* cited by examiner

*Primary Examiner* — Ophelia A Hawthorne
(74) *Attorney, Agent, or Firm* — Quarles & Brady LLP; Yakov Sidorin

(57) ABSTRACT

A methodology for correcting the hip displacement of an injured patient of practically any size with the use of an apparatus assembly structured to enable the helper not only to adjust the thigh vertically (to position the displaced femoral head at substantially the same level as that of the pelvic acetabular fossa) but also to reorient the femur angularly at least with respect to yaw and pitch to ensure reliable application of a lifting traction force to the injured lower extremity to effect the safe and atraumatic return of the dislocated femoral head to the vacated acetabular fossa.

25 Claims, 12 Drawing Sheets

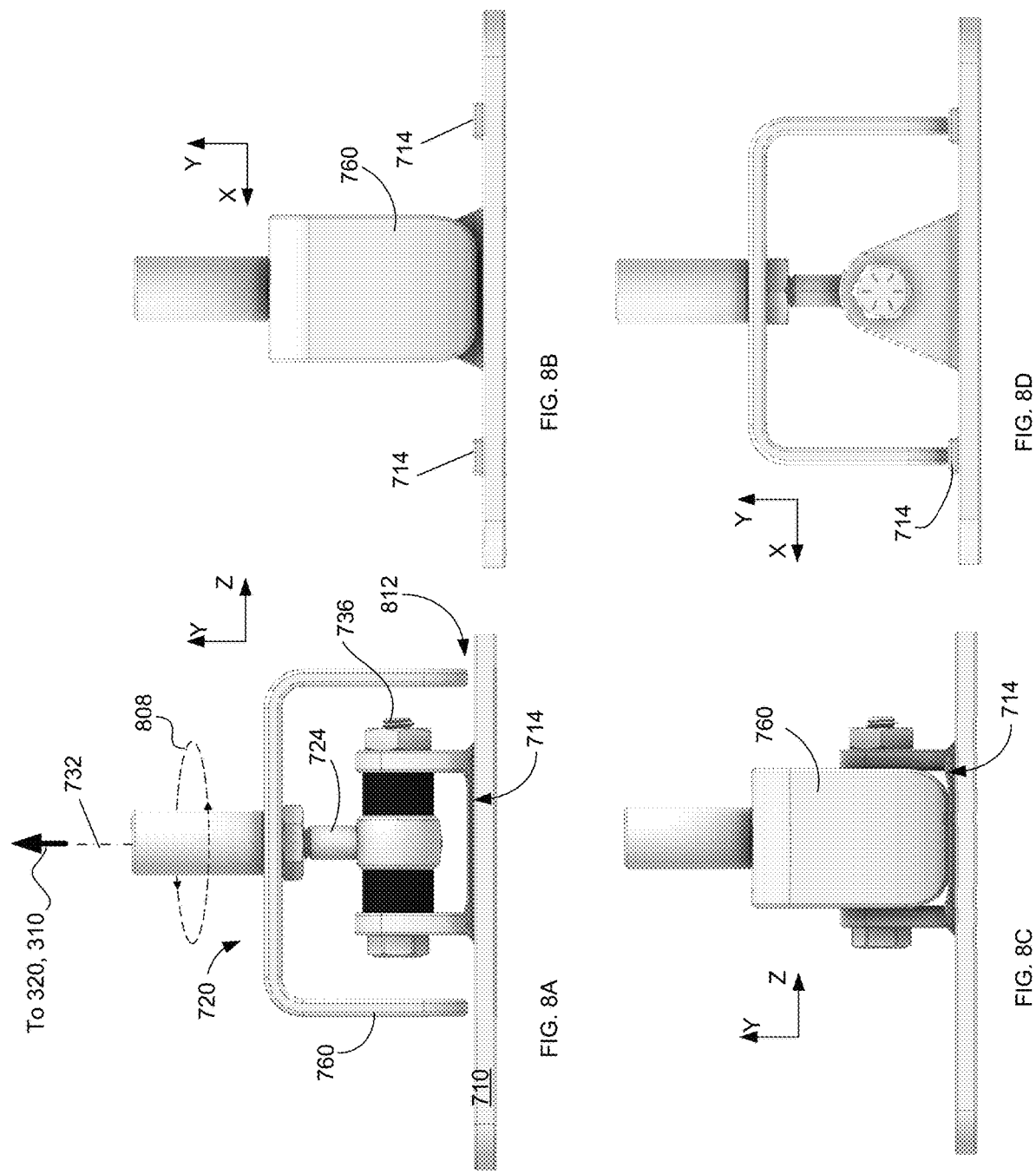

HIP RELOCATION APPARATUS

TECHNICAL FIELD

The present invention relates generally to a methodology of correction for a hip dislocation and, more particularly, to an apparatus configured to make the procedure easier and more reliable for both the patient and the provider.

RELATED ART

The dislocation of the hip joint is a fairly common occurrence, especially among elderly patients fitted with an artificial hip joint. FIG. 1 schematically illustrates the structure of a hip. When a patient falls or moves his or her leg in a certain way, a femur may become dislocated, which is an emergent situation mandating the repositioning of the femur back into its pelvic acetabular fossa as quickly, safely, and efficiently as possible to avoid continued severe pain and possible additional nerve, vascular, ligamentous, muscular, and/or bone injury if the dislocation persists. Radiographs are often taken prior to relocation attempts that determine that the hip is simply dislocated without pre-procedure fracture. In order to reduce (correct) that dislocation, a time-honored maneuver known as the Allis maneuver has been historically applied (see, for example, Dawson-Amoah et al. at ncbi.nlm.nih.gov/pmc/articles/PMC6162140/; or in The Atlas of Emergency Medicine, Chapter 11-21, available at accessmedicine.mhmedical.com/content.aspx?bookid=2969&sectionid=250459150).

This maneuver requires the physician or helper to exert an enormous amount of energy to produce the large force that is necessary to perform the maneuver. Here (in reference to the sketch of FIG. 2), a patient is placed on a bed/supporting surface/examination table/gurney on his/her back, restrained by his/her lower pelvis to such supporting surface. The physician/provider climbs onto and stands upon that supporting surface, flexes the patient's hip to ninety degrees and bends patient's knee to about ninety degrees (placed between the provider's legs). Then the provider grips and tracts with significant force using the provider's body and strength as leverage to elevate the head of the dislocated femur into alignment on a plane with its prior position at the level of the pelvic acetabular fossa, stretching out the still-attached ligaments and muscles, nerves and vessels) in other words, applies steady in-line traction and upward traction substantially simultaneously at the proximal calf, which lifts the femoral head; see arrow 220). Then, the provider internally or externally rotates the head of the femur (that is, adjust it into position) until it goes back (adducted) into its prior placement, usually with a palpable event as the femoral head re-seats. The femur must not be forcefully adducted because this may fracture the femoral head and/or acetabulum. Quite commonly, an anesthetic or sedative medication is given to the patient before the hip relocation is attempted.

The application of this large force places a substantial strain on the physician's back. In addition, most commonly, the required upward force is so great that the physician must stand atop the bed or support (on which the patient is placed) to gain mechanical advantage, which places the doctor and patient in an awkward and unsafe position. The fact that in the Allis maneuver an assistant has to apply downward pressure on the pelvis (while the doctor produces the large traction force needed at the calf) introduces several problems: the procedure requires more than one person; the application of the upward traction force places substantial physical stress on the physician; large force is needed to implement the maneuver, which coerces the provider/doctor to gain mechanical advantage by standing atop the table and above the patient.

An X-ray is typically taken at the end of the procedure to confirm replacement of the femoral head back into the acetabular fossa, and to evaluate for the possibility of a missed fracture or bone injury that was not identified when the femoral head was displaced and then subsequently replaced. Depending on the size of the patient, length of time of the femur being dislocated, previous skeletal surgical or injury history, musculature of the patient, the degree of muscle spasms and perceived pain, the ability of the patient to cooperate, and the strength and fitness of the provider and their own experience and expertise, this may at times be a 'relatively' easy procedure to do. Alternatively, or at other times with other patients and other providers this may be a task that even the strongest and most experienced provider cannot accomplish in the initial emergency room or urgent care setting. As testimony to the rigor and potential risk of the Allis maneuver, other techniques or maneuvers have been advanced (see Bigelow, Stinson, Whistler, Captain Morgan maneuvers) in part to avoid the risk of injury to the provider including back strain or injury or falls.

Notably, in none of these maneuvers is the actual force or pressure of the effort ever measured or recorded, with success assessed simply as the eventual clinical replacement of the femoral head back into the pelvic acetabular fossa at the time of the effort, or not. If the hip cannot be relocated by such efforts, taking the patient to the operating suite where a general anesthetic may be applied to allow enough muscle relaxation for the hip relocation to be accomplished using the same maneuvers might be attempted; failing that, operative intervention may be necessary to replace the head of the femur in the pelvic acetabular fossa.

The well-recognized problems with the hip reduction procedure cause a still unsatisfied need to improve the hip reduction maneuver methodology and enhance the safety of the physician and patient.

SUMMARY OF THE INVENTION

Embodiments of the invention discussed below are structured to resolve the issue and to standardize the methodology of repositioning a patient's dislocated hip in a safe and codified manner with the use of a lightweight, sturdy, reusable, easily maintained, comfortable apparatus that includes a pneumatic or hydraulic length-extending (sub) device and a component structured to provide the injured lower limb with a possibility of being reoriented at least in angular dimensions corresponding to yaw and pitch in order to achieve ease in reliably applying a lifting traction force to the lower extremity of a patient of almost any size, who has suffered a recent hip dislocation. An embodiment of the hip relocation apparatus is lightweight, adjustable to the size of the patient and the patient's extremity, quickly applied with minimal additional distress to the patient, and moveable within desired limits to assist in relocation once the apparatus is applied to support the patient's dislocated limb from below. As the skilled person will readily appreciate from the discussion presented below, the application of an embodiment of the apparatus—and the freedom of movement which it affords a provider of the procedure—safely mimics the efforts of the lifting traction of the conventional Allis maneuver while allowing effective internal or external rotation of the involved leg within the required spatial limits, thereby effectively duplicating the Allis maneuver with the prospect of less risk of injury to either patient or provider. An embodiment of the hip relocation apparatus is structured to provide for immediate release of the lifting traction on the patient's injured leg and interrupting the traction of the apparatus at any step during the procedure if so desired. The embodiment allows for a provider who is physically incapable or unwilling to perform the conventional Allis maneuver or other maneuver—or for a patient who would be considered too large, strong, and/or unwieldy to have his/her hip relocated—to now do so with the minimal necessary force and/or pressure and risk of injury to either the patient or the provider.

To ensure solutions to persisting problems of related art, embodiments of the invention provide a hip relocation apparatus that includes, generally, a leg gutter section or portion, a middle axially extendable section or portion, and a lower structural assembly. The leg gutter section includes a first supporting elongated member and a second supporting elongated member (which elongated members are connected at respective ends thereof to one another at an approximately right angle). The middle axially extendable section has an axis and is structured to reversibly change its spatial extent along the axis, while the lower structural assembly has a swivel bracket and a bracket axle. The swivel bracket is rotatable about the bracket axle, and the bracket axle has an opening extending therethrough transversely to the bracket axle. The bracket axle and a lower end of the middle axially extendable section are configured to be modifiably connectable to one another along the axis with the bracket axle extending substantially parallel to the axis. An upper end of the middle axially extendable section is configured to be disengagingly connected to the leg gutter section to have one of the first and second supporting elongated members be transverse to the axis.

Embodiments of the invention also provide a hip relocation apparatus that includes a leg gutter section, a middle assembly, a lower assembly, and a base apparatus plate. The leg gutter section includes a first supporting elongated member and a second supporting elongated member (which elongated members are connected to one another at respective ends thereof at an approximately right angle). The middle assembly has an axis and is structured to reversibly change its spatial extent along the axis. The lower assembly has a swivel bracket, a bracket axle removably attached to the swivel bracket, and a tilt axle dimensioned to be removably inserted in a throughout opening formed at an end of the bracket axle that is distal to the swivel bracket. (Here, the swivel bracket includes a top bracket portion substantially transverse to the bracket axle; the swivel bracket is rotatable about the bracket axle. A combination of the swivel bracket and the bracket axle is configured to be tiltable about the tilt axle when the tilt axle is inserted in the throughout opening.) The base apparatus plate carries (a) supporting elements that are dimensioned to reversibly secure the tilt axle in a position parallel to and separated from a surface of the base apparatus plate, and (b) at least one stopper element dimensioned to at least temporarily stop at least the swivel bracket from being rotated about the bracket axle when the lower assembly is attached to the base apparatus plate with the use of tilt axle and the supporting elements. In at least one specific implementation of the apparatus, the lower assembly may additionally include a nut on the swivel bracket and/or at least one of the following conditions may be satisfied: (i) a first axial end of the middle assembly is configured to be threadingly attachable to a mating thread of the leg gutter section, and (ii) a second axial end of the middle assembly is configured to be threadingly attachable to the lower assembly via an inner thread of the nut. Substantially in every implementation of the apparatus, the at least one stopper element may be dimensioned to at least temporarily stop a portion of a body of the apparatus from being rotated about the bracket axle when the lower assembly is attached to the base apparatus plate with the use of the tilt axle and the supporting elements (the portion of the body may be formed by (i) attaching the middle assembly to the lower assembly, and/or by (ii) attaching the middle assembly to the lower assembly and attaching the middle assembly to the leg gutter to form a portion of the body). Alternatively or in addition, and substantially in every embodiment of the apparatus, the swivel bracket may be structured to include a top bracket plate and at least one side bracket plate connected to the top bracket plate transversely parallel to the bracket axle (here, the at least one side bracket plate may be oriented to extend along the bracket axle, and the at least one side bracket may be dimensioned to interact with the at least one stopper element during a rotation of the swivel bracket about the bracket axle when the lower assembly is attached to the base apparatus plate with the use of the tilt axle and the supporting elements).

Embodiments of the present invention may be utilized on either one of a patient's dislocated hips when optionally but preferably the beveled leading edge of the sliding rigid support base is placed underneath the patient's injured hip and between the patient's injured hip and the firm surface of an emergency room bed or gurney, with flexion of the patient's hip to about ninety degrees and of the patient's knee to about ninety degrees to fit and place the knee of the patient into the gutter of the apparatus.

Methodology of operation of substantially every of the above-identified embodiments of the apparatus includes at least a step of putting together (assembling) by (a) connecting the leg gutter to a first axial end of the middle assembly and connecting a second axial end of the middle assembly to the lower assembly to have the middle assembly and the lower assembly extend substantially co-axially, and (b) removably attaching the lower assembly to the base apparatus plate with the use of the tilt axle and the supporting elements. The completion of the assembly is followed by placing the base apparatus plate under a patient's leg with a dislocated hip to support the calf of the leg with one of the first and second supporting elongated members in a substantially horizontal orientation. Embodiment of the method additionally includes a step of changing an orientation of the leg secured in the apparatus by at least reorienting a combination of the leg gutter, the middle assembly, and the lower assembly. (Such reorienting includes rotating the combination about the bracket axle, and/or tilting said combination about the tilt axle.) At least one of the embodiments of the method may include a step of reversibly applying a lifting (with respect to the base apparatus plate) force or traction to the leg by changing a length of the middle assembly (optionally, the application of such lifting force or traction includes placing a femoral head and a pelvic acetabular fossa of the leg substantially at the same distance from the base apparatus plate. Alternatively or in addition—and substantially in every implementation—the step of reorienting a combination of the leg gutter, the middle assembly, and the lower assembly may include reversibly and/or temporarily immobilizing the lower assembly with respect to a rotational motion about the bracket axle (optionally, such immobilizing may include positioning a free end of the swivel bracket in contact with and/or over the at least one stopper element). Additionally or in the alternative, and substantially in every embodiment, the method may contain a step of securing the leg in the apparatus by employing first restraining elements to substantially immobilize the calf and the thigh of the leg with respect to the leg gutter and/or employing a second restraining element to limiting a motion of a patient's body with respect to the base apparatus plate.

BRIEF DESCRIPTION OF THE DRAWINGS

The invention will be more fully understood by referring to the following Detailed Description of Specific Embodiments in conjunction with the Drawings, of which:

FIG. 4A illustrates a leg gutter portion of the embodiment of FIG. 3A in perspective view, while

FIG. 6A is an exploded perspective view showing a middle assembly (middle axially extending portion) of the embodiment of the apparatus of FIG. 3A in a withdrawn position, while

FIGS. 8A, 8B, 8C, 8D, 9A, 9B, 9C, and 9D illustrate, in different views and/or positions, at least a part of an embodiment of the lower assembly of the apparatus of FIGS. 3A, 3B.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are depicted in the figures with the understanding that the disclosure is intended to be illustrative, these specific embodiments are not intended to limit the scope of invention the implementations of which are described and illustrated herein.

DETAILED DESCRIPTION

Embodiments of the present invention include apparatus and methods directed to resolving the issue and standardizing the methodology of repositioning a patient's dislocated hip in a safe and codified manner using a lightweight, sturdy, reusable, easily maintained, comfortable, pneumatically or hydraulically and/or manually driven apparatus that makes for ease in reliably applying a lifting traction force to the lower extremity of patients of almost any size who have suffered a recent hip dislocation. The apparatus is lightweight, lends itself to easy adjustment to the size of the patient and the patient's extremity, is quickly applied and may be operable by the only, single medical attendant with minimal additional distress to the patient, and moveable within desired limits to assist in relocation once the hip relocation device assembly is applied to the patient's dislocated limb.

Figure 1:
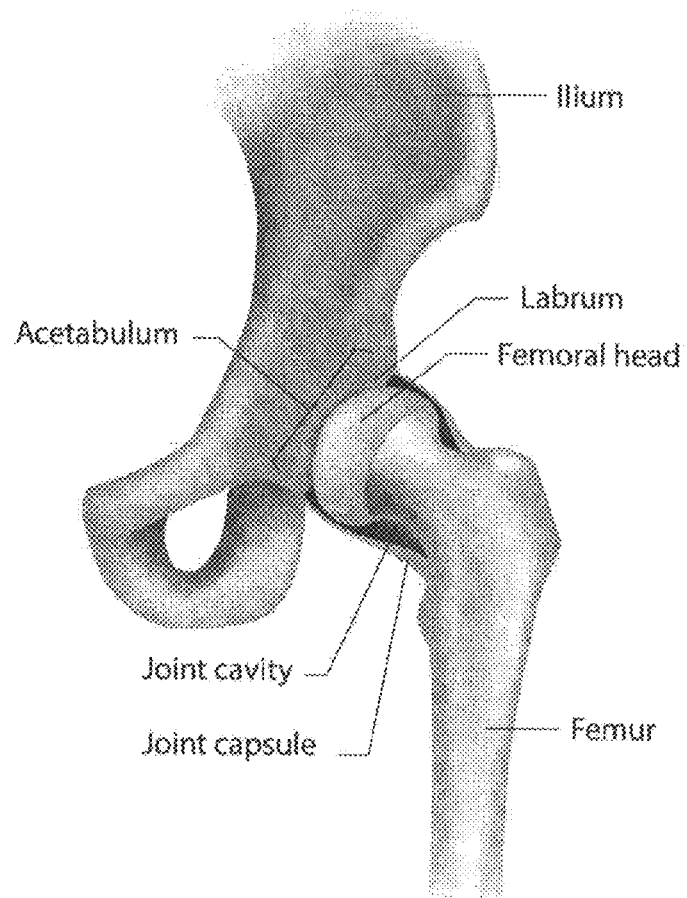
FIG. 1 illustrates schematically structure of a hip joint.
Figure 2:
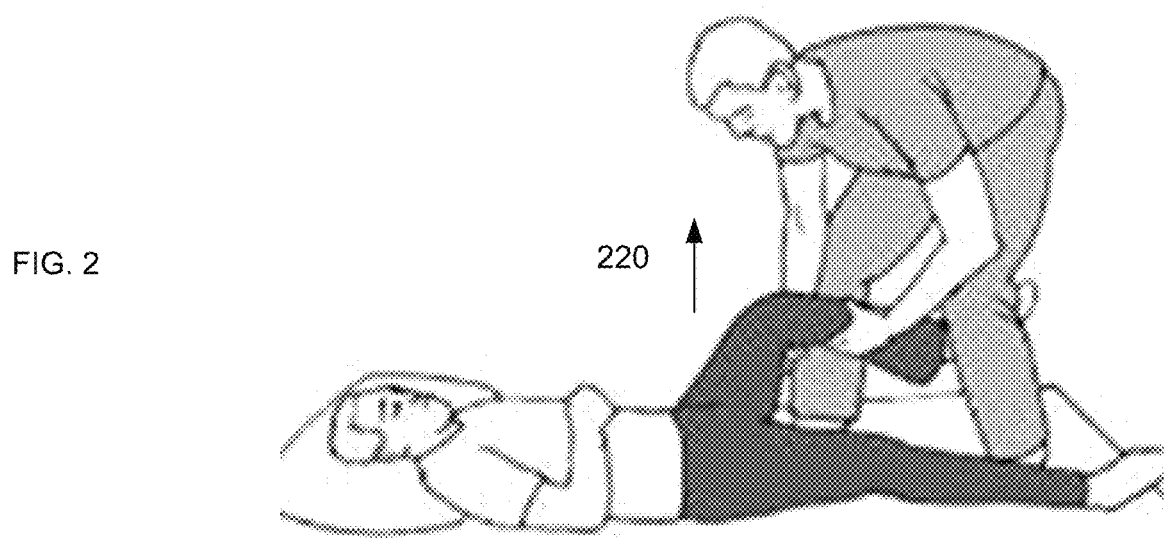
FIG. 2 illustrates the Allis maneuver procedure.
Figure 3A:
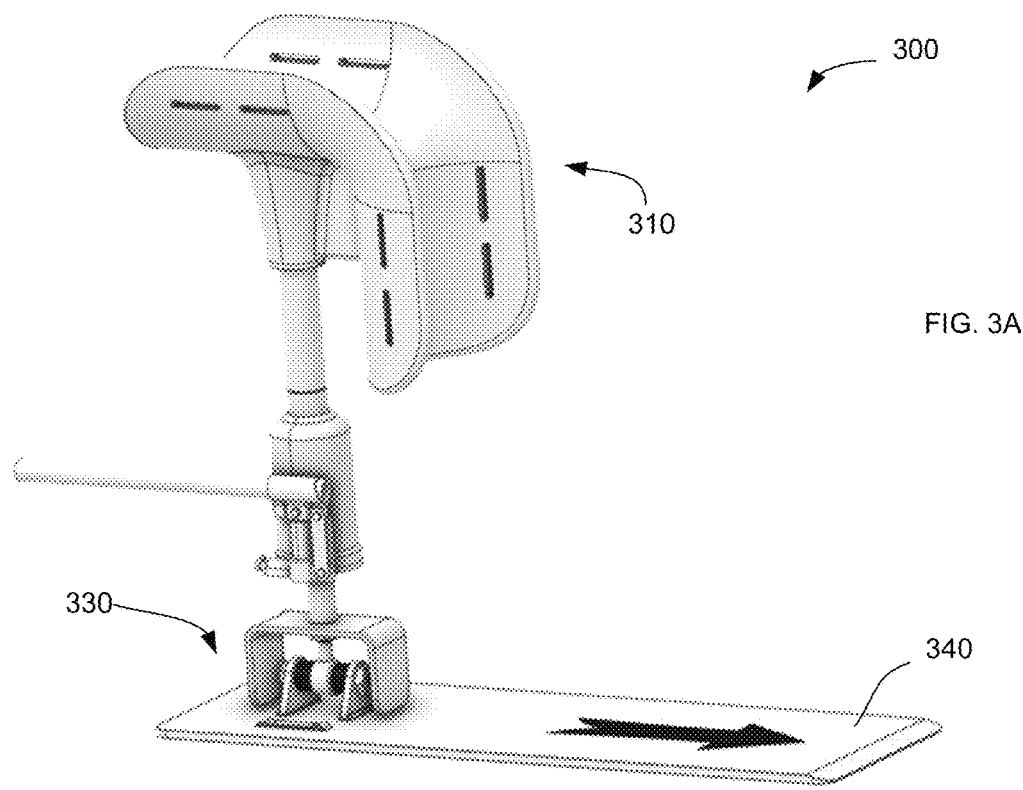
FIG. 3A shows an assembled embodiment of the hip relocation apparatus, while FIG. 3B schematically illustrates the embodiment in exploded view.
Figure 3B:
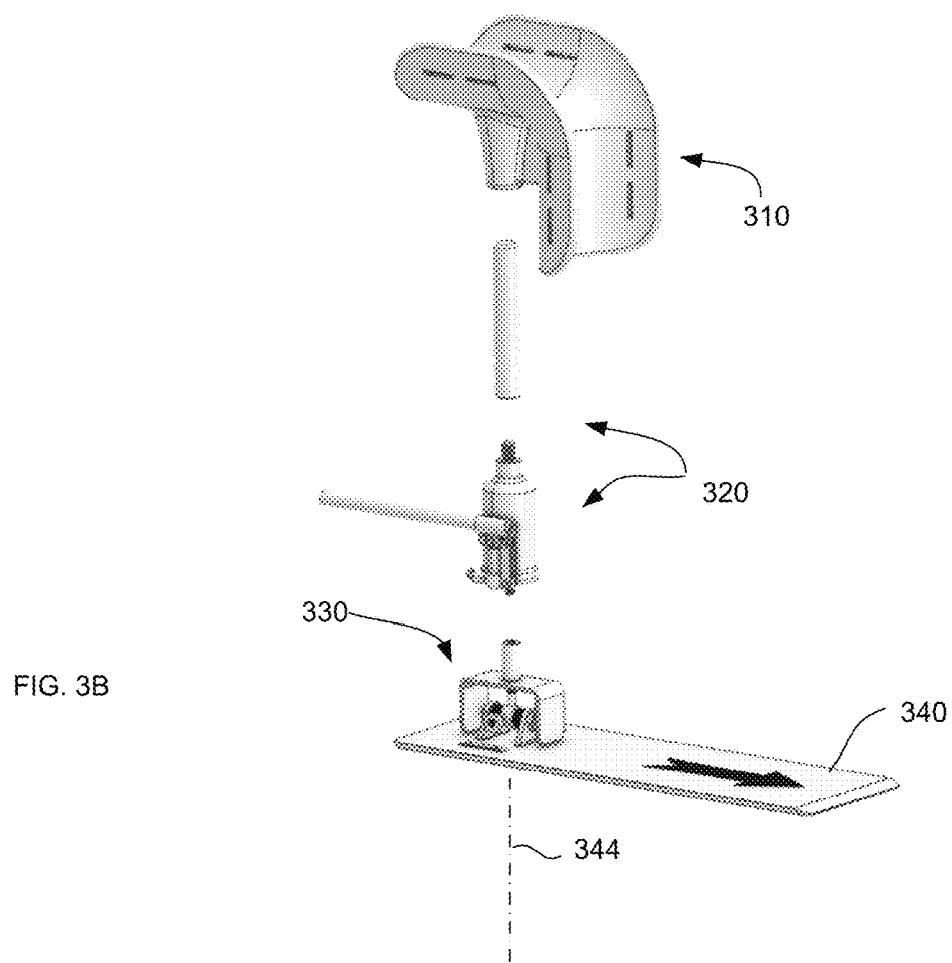
FIG. 3C depicts initial positioning of the embodiment of FIGS. 3A, 3B under and with respect to the injured patient at the initiation of the hip relocation procedure; the patient is shown to be firmly held to the emergency bed or gurney or supporting surface and to the leg gutter portion of the apparatus with belts or restraints.
Figure 3C:
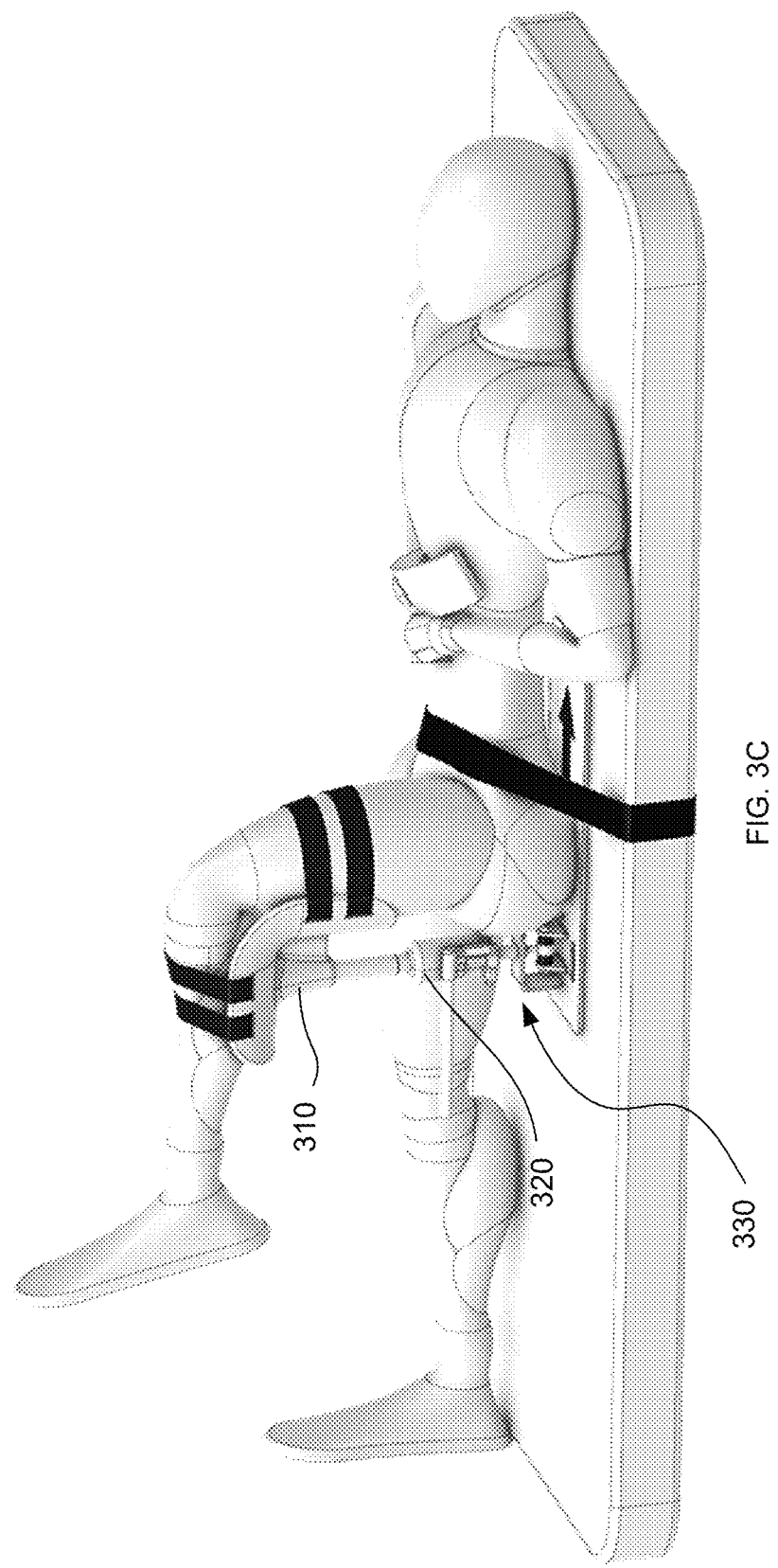

An example of the embodiment 300 of the apparatus structured according to the idea of the invention is shown in FIGS. 3A and 3B, and includes three main portions that are reversibly assembled with one another along the axis 304: a leg gutter portion or section 310, a middle axially extendable portion or section 320 (which may be interchangeably referred to herein as a middle assembly) and a lower structural assembly (lower assembly, for short) 330, which may optionally be additionally secured to the lower base apparatus plate 340 (which, when present, has sufficient spatial extent to be placed under the patient's injured hip and between the patient's injured hip and the firm surface of an emergency room bed or gurney as illustrated in FIG. 3C. As can be seen from the illustration of FIG. 3C and understood from the discussion below, the leg gutter section 310 (which may be optionally padded, to add comfort to the patient) is structured as a leg-securing component of the apparatus 300; the middle assembly 320 is configured as a leg lifting component; and the lower assembly 330 is designed to provide for spatial orientation of the leg of the patient that has been secured in the leg gutter section of the assembled apparatus 300. Additional belts or straps, when used with the leg gutter section 310 and/or in the arc of pelvis (FIG. 3C) may be used to spatially secure the patient and at least to restrict the movement of the patient and/or his/her leg. The axis 344 of the apparatus 300 is schematically illustrated with a dashed line. Various portions of the embodiment 300 are now discussed below in more detail.

Figure 4A:
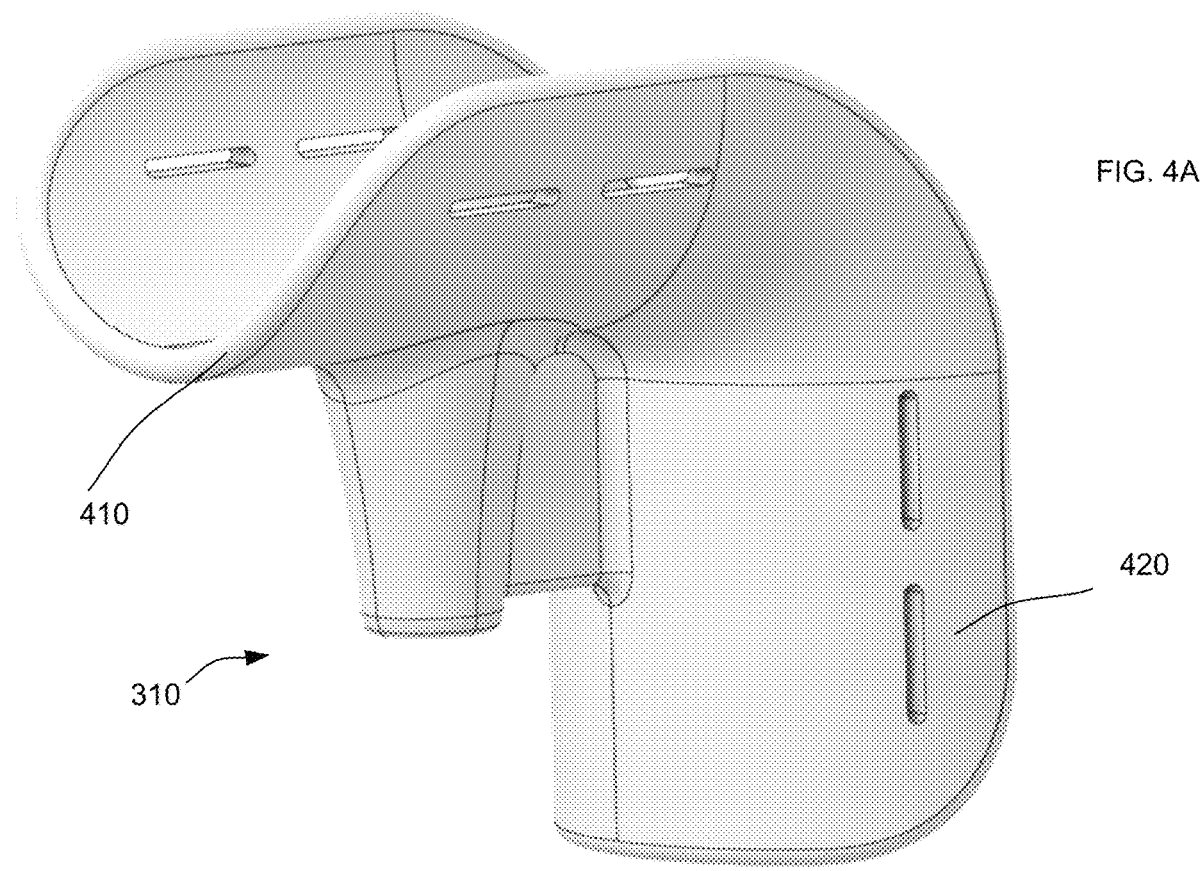
Figure 4B:
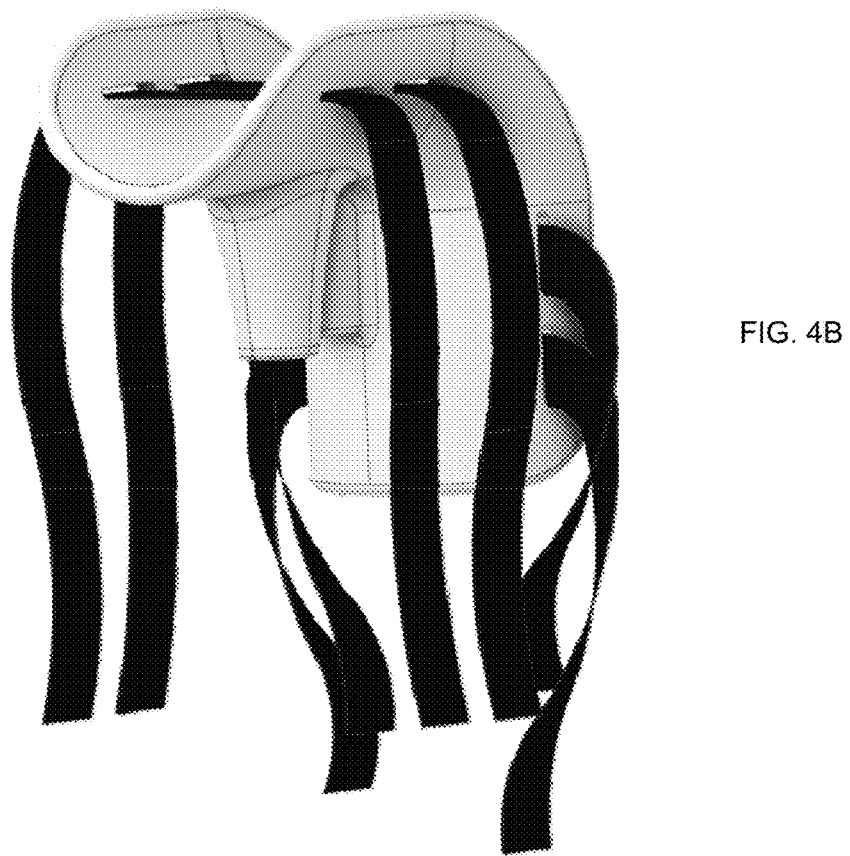
FIG. 4B illustrates the same leg gutter portion equipped with belt or restraint straps for securing the leg placed at the leg gutter portion.
Figure 5A:
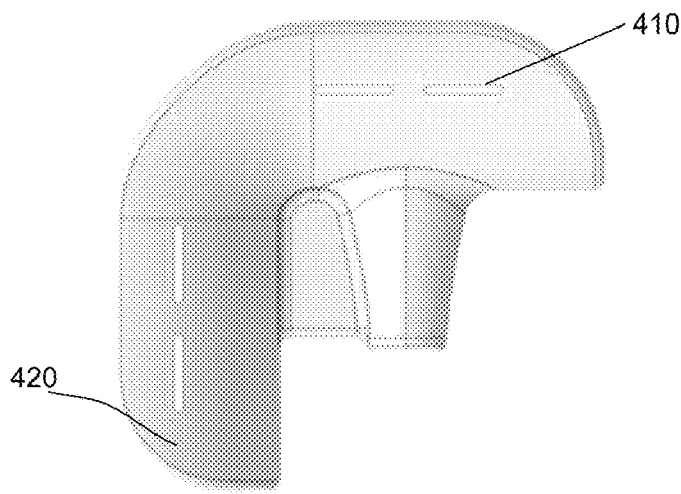
FIGS. 5A, 5B, 5C, 5D, and 5E are different plan and/or elevational views of the embodiment of the leg gutter portion of FIG. 4A.
Figure 5B:
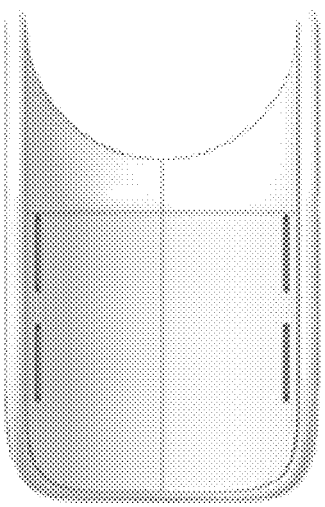
Figure 5C:
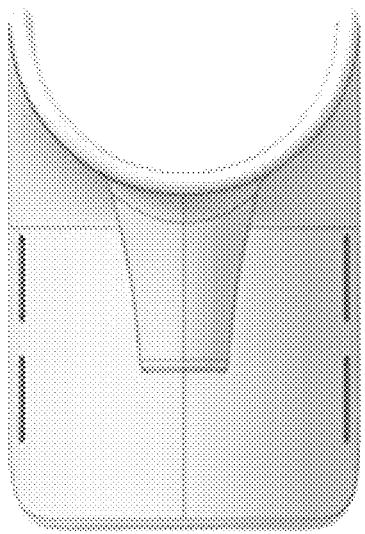
Figure 5D:
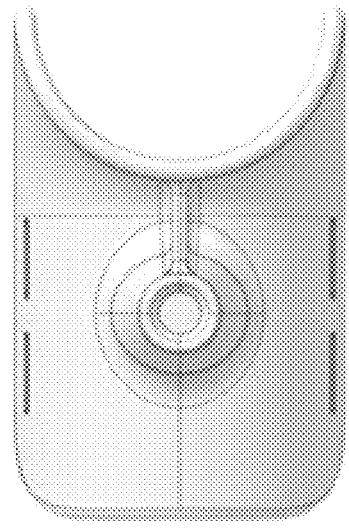
Figure 5E:
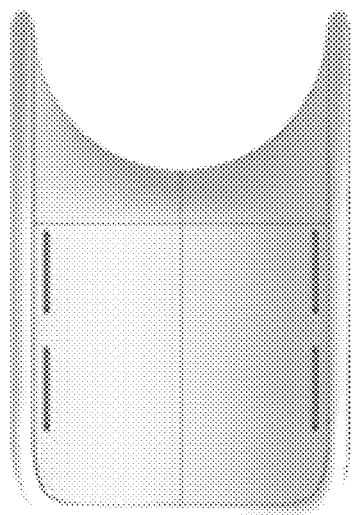

FIGS. 4A, 4B, and 5A through 5E illustrate the leg gutter portion 310 in various views. Specifically, FIGS. 4A and 4B provide perspective views (without and with the securing straps), FIGS. 5A, 5B, 5C, 5D, and 5E provide, respectively, side view, top view, front view, bottom view, and back view. The leg gutter portion 310 generally includes a first leg-supporting elongated member 410 and a second leg-supporting elongated member 420 that are connected at respective ends at an approximately right angle the vertex of which—as can be seen from FIG. 3C—is intended to be placed under the bent injured leg of the patient. Preferably, at least one of the first and second leg-supporting elongated members 410, 420 is shaped as a substantially semitubular channel to comfortably accommodate the appropriate portion of the leg (whether the posterior of the thigh or the posterior of the calf) of the patient. (In addition, the inner surfaces of such semitubular channels may be padded—not shown—to prevent injury to skin or underlying structures that would support the flexed and dislocated limb safely and relatively comfortably.) The leg gutter portion may additionally optionally include a console or gutter spine 430 projecting from both the first and second supporting elongated members 410, 420 in a plane in which the approximately right angle formed by the member 410, 420 is defined to rigidly connect the first and second leg-supporting elongated members to one another. (The term console is defined as and refers to a structural element projecting from a surface to form a bracket.) In order to mechanically cooperate the portion 310 with the middle axially extending portion 320—as discussed below—the leg gutter portion 310 may be equipped with a substantially cylindrically-shaped tubular element 440 that is transversely affixed to one of the members 410, 420. (The tubular element or tube 440 may be optionally rigidly connected with the console 430, as shown in the example of FIGS. 5A through 5E). As shown in FIG. 4B, the leg gutter portion 310 has provisions for straps or belts 450 structured to accommodate and confine the leg within the structure of the portion of the rigid leg gutter 310 so that lifting forces may be applied to the structure of the leg gutter 310 containing the patient's dislocated limb (from below, via the use of the middle axially extending portion 320, as discussed below) rather than to the limb itself (as is currently done during the Allis maneuver). Such straps or belts are passed through the gutter strap anchors portions of the leg gutter 310 (which are shown in the Figures shaped as through slots). In at least one implementation, the mechanical connection between the leg gutter section 310 and the middle assembly 320 is arranged via a thread, in which case the tubular member 440 may be internally threaded.

Figure 6A:
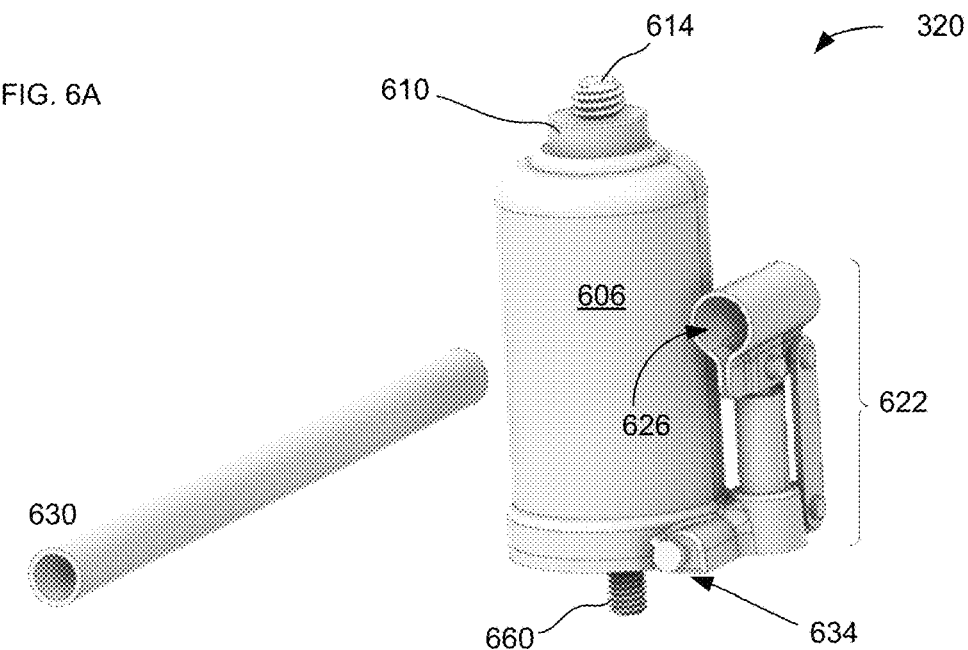
Figure 6B:
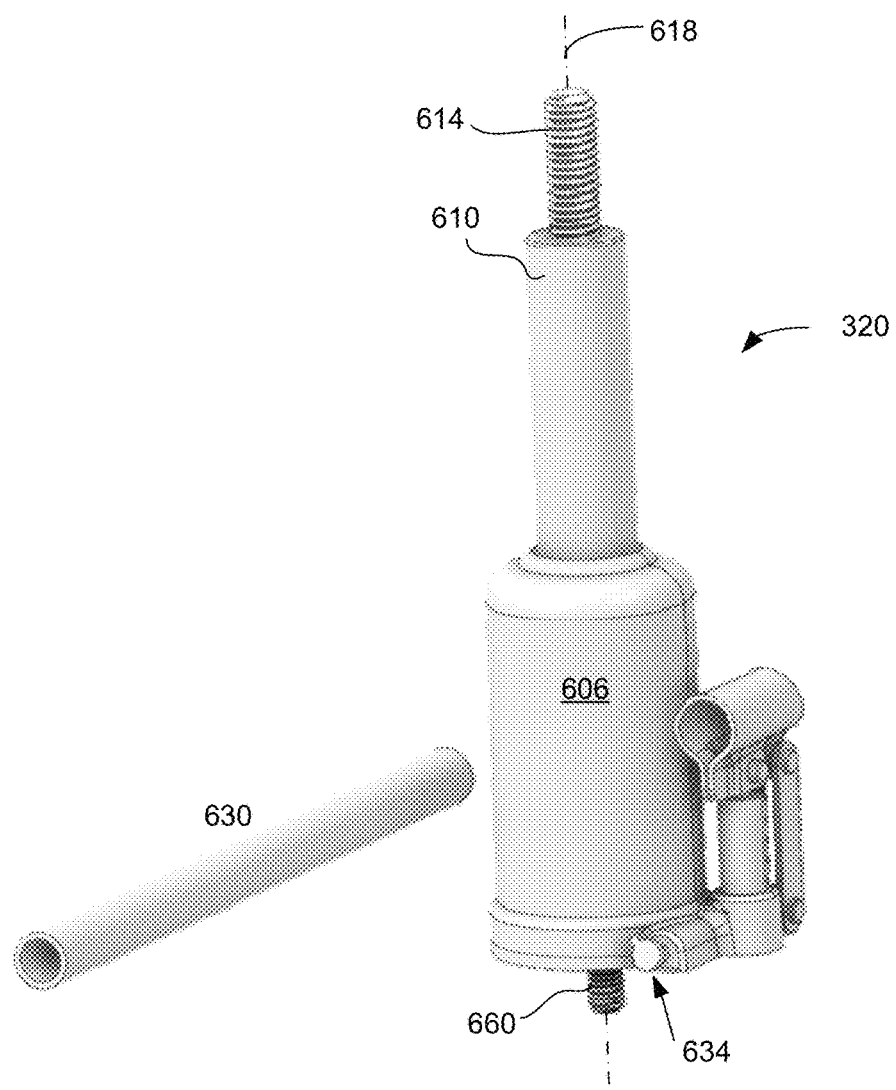
FIG. 6B is a similar view of the middle assembly in an extended position.
Figure 6C:
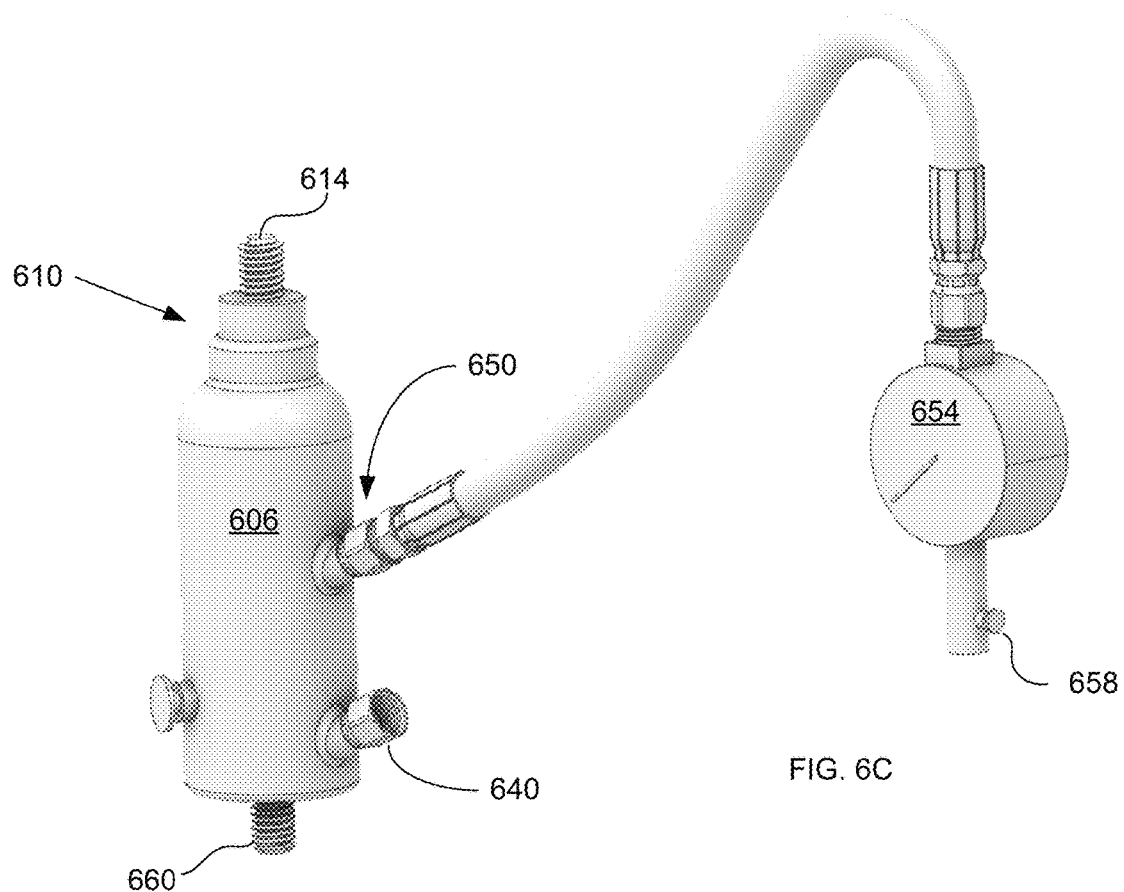
FIG. 6C is a perspective view of a related implementation of the middle assembly.

FIGS. 6A, 6B, 6C provide perspective views of related embodiments of the middle axially extendable portion or assembly 320 of the apparatus 310. The middle assembly 320 is equipped with a pneumatic or hydraulic reservoir 606. The middle assembly 320 also includes at least one pneumatic or hydraulic piston 610 carrying a spatially expandable upper threaded end 614. In FIG. 6A, both the piston 610 and the upper threaded end 614 are shown in a withdrawn (with respect to the reservoir 606) positions, while in FIG. 6B both the piston 610 and the upper threaded end 614 are shown extended from the reservoir 606. When at least one of the piston 610 and the upper end 614 is in a corresponding withdrawn position, the middle assembly 310 operates to lower the leg gutter section 310 (the substantially cylindrical tubular element 440 of which is threadingly affixed to the end 614) with respect to the reservoir 606, thereby reducing the axial extent of the middle assembly 320 altogether along the axis 619 of the assembly 320. When at least one of the (one or more) piston(s) 610 and the upper end 614 is in a corresponding extended position, the middle assembly 310 operates to, respectively, raise the leg gutter section 310, thereby increasing the axial extent of the middle assembly 320. The operation of axial extension and/or withdrawal of the piston(s) 610 may be achieved with the used of the built-in pump 622 of the assembly 310.

Figure 6D:
FIG. 6D shows a set of threaded pistons for use in an embodiment of the middle assembly.

In the specific embodiment shown in FIGS. 6A, 6B, the pump 622 may be complemented with the pump handle portal 626, the pump handle 630 dimensioned to be reversibly inserted into the portal 626, and a reservoir release valve 634. As seen in a perspective view of a related embodiment of FIG. 6C, the reservoir 606 may be equipped with a pneumatic or hydraulic connector 640 configured to be attached to an outside source of pneumatic or hydraulic pressure, manual air pump or compressed air, or an external manual or electric hydraulic pump (not shown for simplicity of illustration). In either of the embodiments of FIG. 6A, 6B or 6C, the pneumatic or hydraulic pump reservoir 606 may also be complemented with a pressure gauge connector (shown in the example of FIG. 6C as 650) that allows a pressure gauge 654 to monitor pressure within the pneumatic or hydraulic pump reservoir 606, with a hand-operated reservoir pressure relief valve 658 that is accessible to the operator at any time. Notably, substantially every embodiment of the middle assembly 320 may be additionally equipped with the threaded shaft (shown as 660) at the base of the pneumatic or hydraulic reservoir 606 dimensioned to facilitate structural mating of the assembly 320 with the appropriate portion (such as a substantially cylindrical threaded metal tubing) of the rigid lower structural assembly 330. In the specific case when the middle assembly 310 includes a multiplicity of pneumatic pistons 610, such pistons may be configured as a set of bodies (shown in FIG. 6D as set 650 including pistons 650(1) through 650(N), N≥2, which may have different lengths and/or different outer diameters) with cylindrically shaped respective inner hollows dimensioned such that a smaller member of the set 650 fits inside a larger member of the set 650 to extend/withdraw the pistons 650(i) telescopically from one another along the axis 618.

Overall the skilled person understands that the middle axially extendable portion or assembly 320 may generally include an airjack component and/or a hydraulic jack component and/or a mechanical jack component as well as a telescopic mechanical component that is complemented at a free upper end thereof with an upper axially repositionable bolt and/or that is configured to be extending axially from a lower base portion of the middle axially extendable section 310. (When the upper axially repositionable bolt such as the upper threaded end 614 is present, the leg gutter portion 310 may be structured to include the internally-threaded cylindrically-shaped tube such as the tubular element 440 transversely affixed to one of the first and second supporting elongated members 410, 420 of the leg gutter 310. In this case, a thread of the axially repositionable bolt and an internal thread of the cylindrically-shaped tube are preferably mating threads.)

As used in this disclosure and for the purposes of the appended claims, the term airjack (device) component or a similar term is defined as and refers to a mechanism configured to extend a length of a chosen element or section with the use of an inflatable support; the term hydraulic jack component or a similar term is defined as and refers to a device configured to extend the length of the section by applying a force via a hydraulic cylinder; the term mechanical jack component is defined as and refers to: a mechanism configured to extend the length of the second with physical means, such as a motor or hand-operated lever (examples are provided by a screw jack, a house jack, a scissor jack as known in related art).

One example of construction of the lower assembly 330 of the embodiment 300 of the apparatus of the invention is now discussed in reference to FIGS. 7A, 7B, 7C, 8A, 8B, 8C, 8D, 9A, 9B, and 10A, 10B.

Figure 7A:
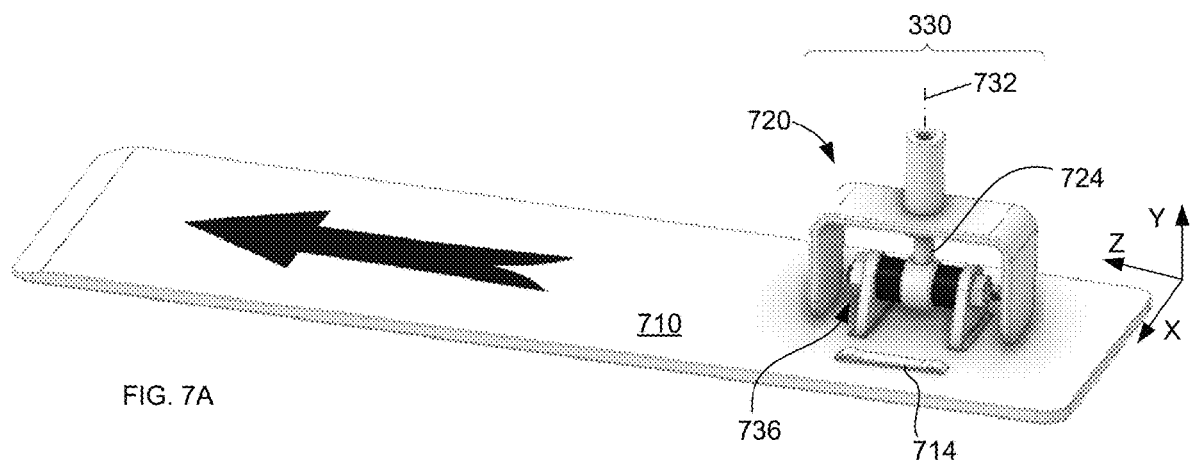
FIGS. 7A, 7B, and 7C are different views of a specific embodiment of the lower assembly (of the apparatus of FIG. 3A) secured at a base apparatus plate.
Figure 7B:
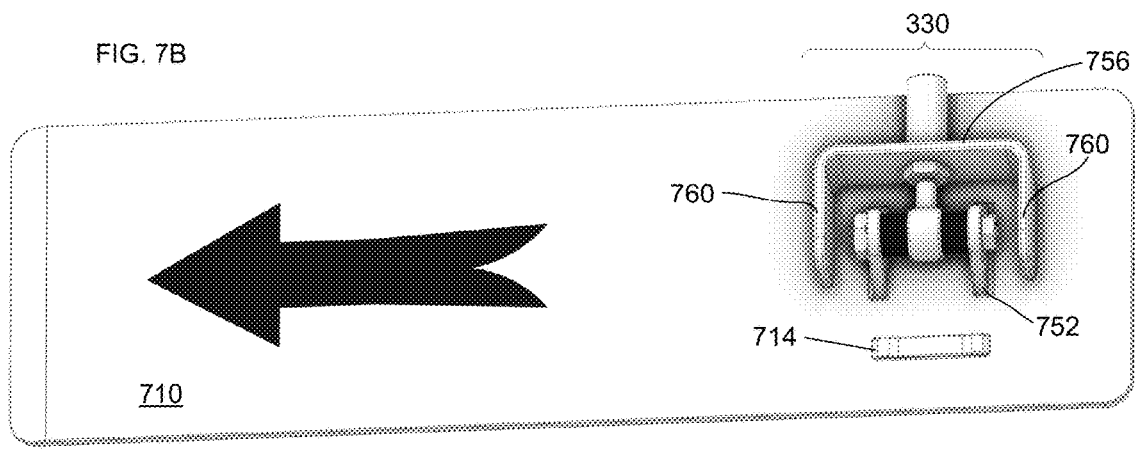
Figure 7C:
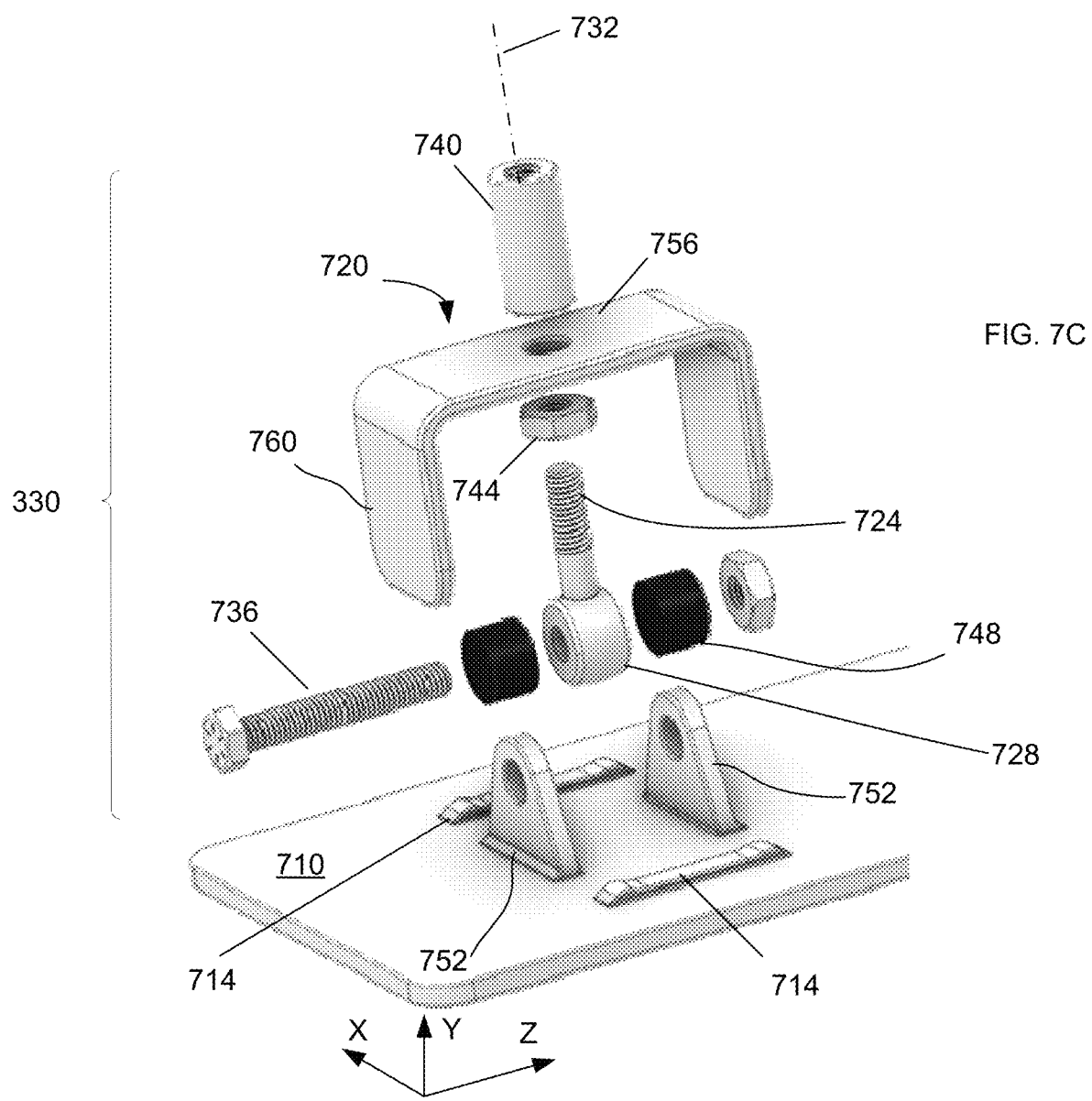

In reference to FIGS. 7A, 7B, and 7C, presenting in different perspective views the implementation of the lower assembly 330 (the local Cartesian system of coordinates is as indicated), such lower assembly may be in at least one case affixed to (supported from below by) the generally rigid base apparatus plate 710 carrying generally chamfered rises 714 on both sides of the assembly 330. Further discussion is that of such specific case when the base apparatus plate 710 is present, for certainty, but describes the structure of the lower assembly in general as well.

The lower assembly 330 generally includes a swivel bracket 720 and a bracket axle 724 (which in one case may be dimensioned as a bolt and/or a threaded member) about which the swivel bracket 720 (and everything that is affixed to it) is configured to be reversibly rotatable. The bracket axle may have, at an end thereof that is distal/opposing to the swivel bracket 720, an opening 728 that extends through the axle 724 substantially transversely to the axle 724.

The following portion of the disclosure describes a specific implementation of the lower assembly 330, which employs a component referred to as a tilt axle. The skilled artisan will readily appreciate, however, that alternatives to the tilt axle can be employed which, structurally, may be dimensioned as a variety of a ball-and-socket joint, for example (whether a condyloid joint, or a saddle joint, or a hinge joint, or a pivot joint, as known in the art). Overall, therefore, the construction of the lower assembly 330 according to the idea of the invention employs a tilt joint (which in one implementation may be structured with the use of a tilt axle, as discussed below, and in another—with the use of a conventional ball-and-socket joint).

The swivel bracket 724 is made to be not only rotatable about the axle 724 (that is, about the axis 732 that is substantially parallel to the bracket axle 724) but also reversibly tiltable about the tilt axle 736 that is passing through the opening 728. To this end, FIG. 7B illustrates the situation in which the combination of the swivel bracket 720 and the bracket axle 724 of the lower structural assembly 330 is tilted about the tilt axle when the tilt axle 736 to the point that the side surface of the bracket 720 is substantially parallel to and/or in contact with the surface of the base apparatus plate 710. The bracket axle and a lower end of the middle assembly 320 are made modifiably connectable to one another along the axis 732, as discussed below in more detail.

The bracket axle 724 may be held by a cylindrical threaded metal tubing portion 740 and a nut 744 and, optionally, may be stabilized with thick rubber washers 748 and stabilizing panels (support elements) 752 that may be irreversibly welded to the base plater 710 and held as a group by an appropriate set of affixing elements (one of which, as shown, is the tilt axle 736).

In the example of FIGS. 7A-7C, the swivel bracket is shown to include a top bracket plate 756 and at least one (as shown—two) side bracket plate 760 connected to the top bracket plate 756 transversely parallel to the bracket axle 724, with the bracket axle 724 passing substantially through a center of the top bracket plate 756.

The lower edges of the swivel bracket 720 are designed to engage the chamfered risers 714 during the rotation of the swivel bracket about the axle 724 to temporarily/reversibly immobilize/stabilize/lock the lower assembly 330—and, with it, the overall hip reduction apparatus 300—with respect to its rotational motion in the azimuthal plane that is, about the axes 618, 732. The base apparatus plate 710 may contain indicia (such as a centering directional arrow, as shown) devised to guide the provider in locating placement of the plate 710 directly beneath the dislocated hip (see FIG. 3C); the leading edge of the base apparatus plate 710 in this case may be tapered (as shown) to facilitate insertion of the base plate between the patient and the underlying supporting surface.

FIGS. 8A, 8B, 8C, and 8D illustrate the lower assembly in different spatial positions and/or orientations, with the arrow 808 schematically showing one possible direction of rotation of the bracket 720 (together with the cylindrical tubing portion 740 and, therefore, together with the middle assembly 320 and the leg gutter portion 310 when the apparatus 330 is fully assembled) about the axis 732.

As shown in FIG. 8A, the lower assembly 330 is oriented such that the plane defined by edge surface of the bracket 720 (which corresponds to the plane of FIG. 8A, the yz-plane) is substantially parallel to the longitudinal extent of the riser(s) 714 along the local z-axis, while the axis 732 (and the bracket axle 724 being substantially perpendicular to the upper surface of the base apparatus plate 710. In this position, the bracket 720 (and, with it, the lower assembly 330) is substantially "unlocked" as dimensions of the side bracket plate(s) 760 of the swivel bracket 720 provide for a gap 812 between free end(s) of the side bracket plate(s) and the nearest surface. Being unlocked, the swivel bracket 720 is free to be both rotated about the axis 732 (and the axle 724) and tilted about the axle 736. FIG. 8B illustrates this position/orientation of the assembly 330 in a plan view as seen along the z-axis. When, during the azimuthal rotation (arrow 808) the free end(s) of the side bracket plate(s) 760 encounter the riser(s) 714 and are moved on top of the riser(s)—as shown in FIGS. 8C, 8D—the free end(s) of the side bracket plate(s) 760 of the swivel bracket 720 are releasingly retained on top of the riser(s) 714 (due to friction, for example). In this orientation/position, any further rotational motion of the bracket 720 (together with the cylindrical tubing portion 740 and other portions of the apparatus 300 attached to the bracket 720 via such tubing portion 740) in the azimuthal plane (the local xy-plane) is temporarily prevented and/or frictionally restricted (that is, at least the lower assembly 330 is in a "locked" position) at least until a rotational force, applied to the lower assembly 330 (the bracket 720) exceeds a force of static friction. (In static friction—as is well recognized and accepted in related art—the frictional force resists a force that is applied to an object, and the object remains at rest until the force of static friction is overcome by the applied force.)

Figure 9A:
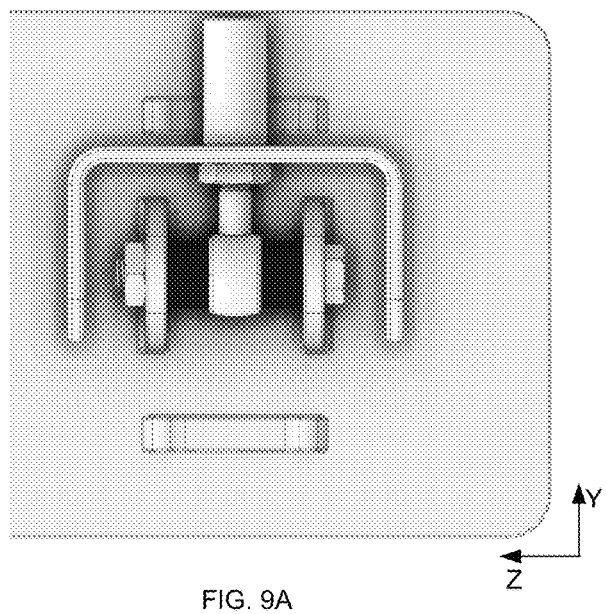
Figure 9B:
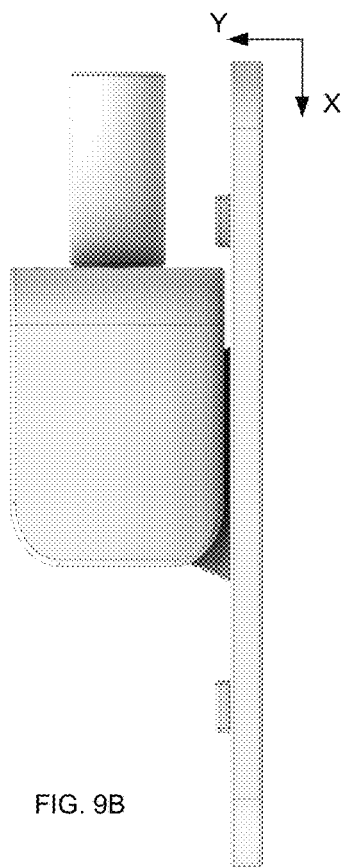
Figure 9C:
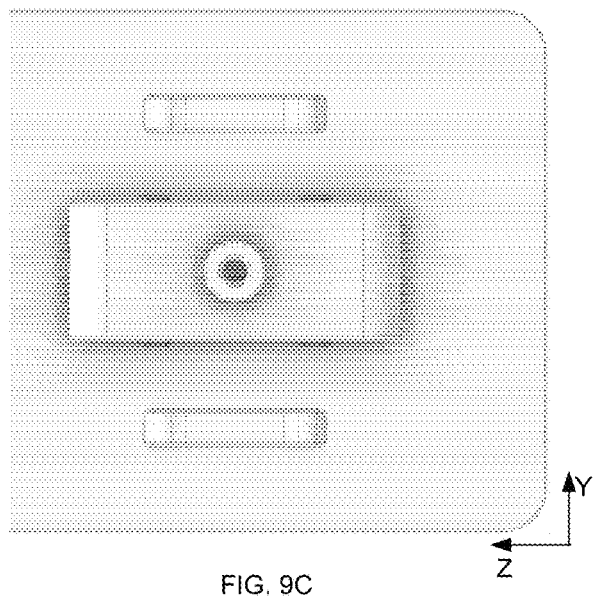
Figure 9D:
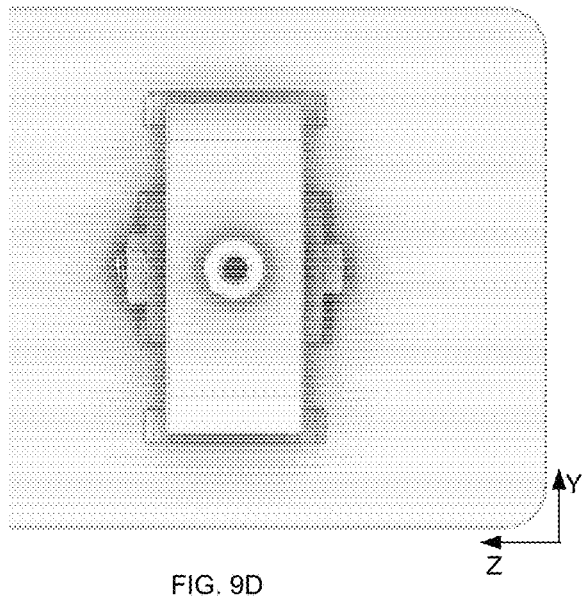

FIGS. 9A, 9B schematically illustrate the lower assembly 330 in an unlocked position when swivel bracket 720 together with the bracket axle 724 are tilted about the axle 326 at a substantially right angle, while FIGS. 10A, 10B provide top views of the lower assembly 330 respectively corresponding to the views of FIGS. 8A and 8D. The reversible affixation/assembly of the lower assembly portion 330 and the middle assembly portion 320 of the apparatus 300 may be carried out by bolting the threaded member 660 into the matingly corresponding inner thread of the tubular element 740.

The skilled person now understands that the combination of the structure of the lower assembly 330 and the presence of the motion restricting elements such as riser(s) 714 affords the assembled apparatus at least degrees of rotational freedom that correspond to yaw and pitch, while the reversible extension of the axial length of the middle assembly 320 provides for rise or lowering of the leg gutter portion 310. Aggregately, these degrees of freedom of movement allow the provider slowly and without applying any substantial force to manipulate the injured leg of the patient, secured in the leg gutter, to align the head of the dislocated femur at the level of the pelvic acetabular fossa, prior to repositioning it into the proper position with a substantially small laterally applied force.

The skilled person will readily appreciate that use of the embodiment of the hip relocation apparatus may be optionally simplified if, prior to handling the injured leg of the patient, the target working axial extent of the assembled apparatus 300 is approximated or assessed by positioning the assembled apparatus with its axis 344 being substantially vertical, orienting the thigh of the uninjured leg of the laying patient substantially vertically along the axis 344 of the apparatus and along the vertically-extending semitubular (that is, shaped substantially as half a tube divided longitudinally) channel portion of the leg gutter 310, placing the calf of this uninjured leg in the horizontal semitubular channel of the leg gutter portion 310, and withdrawing or extending the piston(s) 610 and/or upper threaded end 614 of the middle assembly 320 until the crus of this leg is also substantially horizontal. The degree to which the middle extendable section was adjusted during such a procedure provides the person operating the apparatus with a good approximation of the length of the middle extendable section that would be required when employing the apparatus on the injured leg to align the pelvic acetabular fossa and the femoral head displaced from it due to the hip injury at approximately the same level prior to correcting the hip displacement by inserting the femoral head into the acetabular fossa.

Overall, a skilled artisan having the benefit of this disclosure can readily appreciate that embodiments of the invention provide a hip relocation apparatus that generally includes a leg gutter portion or section, a middle axially extendable portion or section, and a lower structural assembly. The leg gutter section includes a first supporting elongated member and a second supporting elongated member (which supporting elongated members are connected at respective ends thereof to one another at an approximately right angle). The middle axially extendable section has an axis and is structured to reversibly change a spatial extent thereof along the axis. The lower structural assembly has a swivel bracket, and a bracket axle (here, the swivel bracket is rotatable about the bracket axle, and the bracket axle has an opening extending therethrough transversely to the bracket axle; the bracket axle and a lower end of the middle axially extendable section are configured to be modifiably connectable to one another along the axis with the bracket axle being substantially parallel to the axis; an upper end of the middle axially extendable section is configured to be disengagingly connected to the leg gutter section to have one of the first and second supporting elongated members be transverse to the axis. In at least one specific embodiment of the apparatus, the first supporting elongated element may include a substantially semitubular channel and the second supporting elongated element includes a second substantially semitubular channel and/or at least one of the following conditions may be satisfied: (a) the leg gutter section includes a console projecting from both the first and second supporting elongated members in a plane in which the approximately right angle is defined and rigidly connecting the first and second supporting elongated members to one another; and (b) the leg gutter section comprises a cylindrically-shaped tube transversely affixed to one of the first and second supporting elongated members. (When condition (b) is satisfied, such cylindrically-shaped tube is preferably internally threaded. When the leg gutter section includes the internally-threaded cylindrically-shaped tube transversely affixed to one of the first and second supporting elongated members, a thread of the axially repositionable bolt and an internal thread of the cylindrically-shaped tube are preferably mating threads.) Alternatively or in addition, and substantially in every implementation of the apparatus, the middle axially extendable section may be structured to be telescopically extendable along the axis (and, to effectuate such telescopic extension, may optionally include an airjack, a hydraulic jack, and/or a mechanical jack. In at least one specific implementation of the apparatus, a telescopic mechanical component of the middle axially extendable section may be complemented with an upper axially repositionable bolt and/or may be structured to extend axially from a lower base portion of the middle axially extendable section. In at least one implementation, when the middle axially extendable section includes a threaded shaft, the lower structural assembly preferably includes a nut affixed to the swivel bracket (the nut has a nut thread that is dimensioned to be mated with a thread of the threaded shaft. Additionally or in the alternative—and substantially in every implementation—the apparatus may include a base apparatus plate configured to carry support elements secured on a surface thereof (the support elements being configured to removably secure a tilt axle substantially parallel to and separated from the base apparatus plate), and the combination of the swivel bracket and the bracket axle of the lower structural assembly is configured to be reversibly tilted about the tilt axle when the tilt axle is passed through the opening and removably secured at the support elements of the base apparatus plate. Alternatively or in addition—and substantially in every implementation of the apparatus—the swivel bracket may be structured to include a top bracket plate and at least one side bracket plate connected to the top bracket plate transversely parallel to the bracket axle (the bracket axle passing substantially through a center of the top plate with the opening being distal to the top bracket plate). When the swivel bracket is so structured, the base apparatus plate preferably additionally includes at least one motion restricting element affixed to the surface of the plate, and relative spatial coordination of the at least one motion restriction element and the support elements is such that the at least one side bracket plate is reversibly stopped by the at least one motion restricting element during rotation of the swivel bracket about the bracket axle when of the following conditions are met: (i) the swivel bracket includes a top bracket plate and at least one side bracket plate connected to the top bracket plate transversely parallel to the bracket axle, and (ii) the combination of the swivel bracket and the bracket axle of the lower structural assembly is reversibly attached to the base apparatus plate by having the tilt axle pass through the opening and removably secured at the support elements of the base apparatus plate. In at least the latter case the swivel bracket and the at least one motion restricting element may be configured to ensure that (when the lower structural assembly is reversibly secured to the base apparatus plate via the tilt axle) a free end of the at least one side bracket plate, during the rotation of the swivel bracket about the bracket axle, is positioned on top of the at least one motion restricting element and is frictionally restricted from sliding off of or being separated from the at least one motion restricting element unless a rotational force (applied to the swivel bracket) exceeds a force of static friction.

Examples of dimensions of at least one practical implementation of the apparatus discussed above are as follows: the vertical extent of the reservoir 606 is about 9.5" (and generally from 8" to 10"); the overall distance between the top of the reservoir 6006 and the horizontal surface of the leg gutter 310 on which a leg is positioned (which includes an typical extent of the piston 610) is about 12" (and generally between 10" and 14") and the vertical extent of the lower structural assembly is about 5" (and generally between 4" and 6") such that the overall axial extent of the assembled apparatus, measured between the surface of the board 340 and the horizontal surface of the leg gutter 310, is about 26.5" (generally, between 24" and 28"). The size of the board 340 is about 6" by 20", while the width of the swivel bracket 720 limited by the bracket plates 760 is about 3.5" (generally, between 3" and 5"). While specific values chosen for this embodiment are recited, it is to be understood that, within the scope of the invention, the values of all of parameters may vary over wide ranges to suit different applications.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

Figure 10:
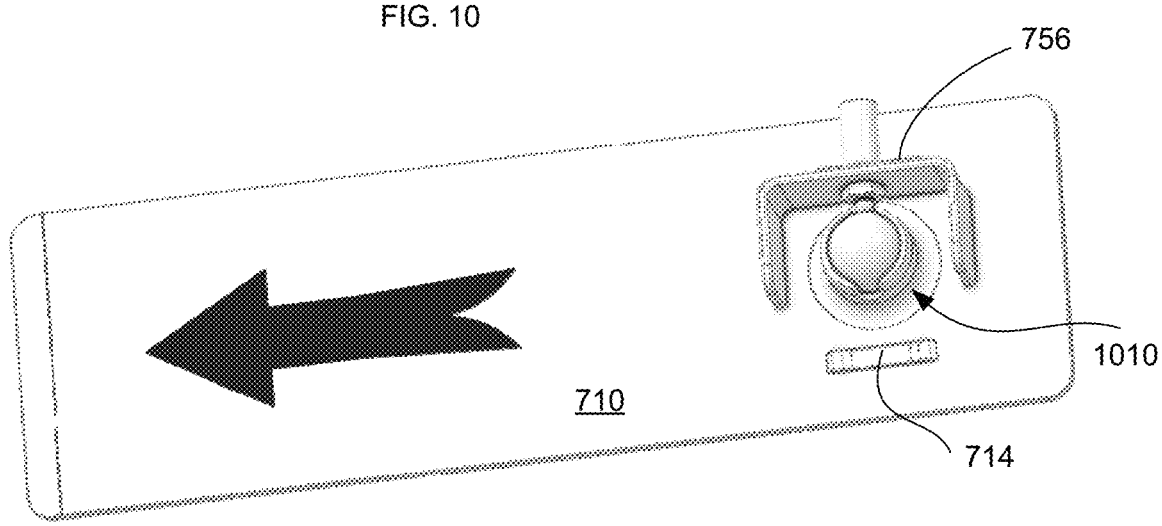
FIG. 10 is a schematic illustration of a related embodiment of the lower assembly, employing a tilt joint configured as a ball-and-socket joint.

Understandably, structural variations of components of the apparatus that do not substantially change its operational performance remain within the scope of the invention. For example, the lower structural assembly can be constructed with the use of a ball-and-socket joint 1010, as schematically shown in FIG. 10, for example.

It is also appreciated that removable connections and mechanical engagements between constituent components of an given embodiment of the apparatus—such as, for example, a mechanical engagement between a piston 610 and the leg gutter 310—can be configured both with the use of a thread (in a discussed example—with the use of the bolt 614) and without a thread, via an unthreaded fitting as recognized in related art.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself. The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

For the purposes of this disclosure and the appended claims, the expression of the type "element A and/or element B" is defined to have the meaning that is equivalent to "at least one of element A and element B".

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

What is claimed is:
1. A hip relocation apparatus comprising:
   a leg gutter section including a first supporting elongated member and a second supporting elongated member, the first and second supporting elongated members connected at respective ends thereof to one another at an approximately right angle;
   a middle assembly having an axis and structured to reversibly change a spatial extent thereof along the axis,
   a lower assembly having a swivel bracket, a bracket axle removably attached to the swivel bracket, and a tilt joint dimensioned to be affixed to an end of the bracket axle that is distal to the swivel bracket,
      wherein the swivel bracket includes a top bracket portion substantially transverse to the bracket axle,
      wherein the swivel bracket is rotatable about the bracket axle,
      wherein a combination of the swivel bracket and the bracket axle is tiltable with respect to the tilt joint; and
   a base apparatus plate carrying thereon (a) supporting elements that are dimensioned to reversibly secure the tilt joint in a position separated from a surface of the base apparatus plate, and (b) at least one stopper element dimensioned to at least temporarily stop at least the swivel bracket from being rotated about the bracket axle when the lower assembly is attached to the base apparatus plate with the use of the tilt joint and the supporting elements.
2. A method comprising:
   assembling the apparatus according to claim 1, wherein the tilt joint includes a tilt axle dimensioned to be removably inserted in a throughout opening formed at the end of the bracket axle that is distal to the swivel bracket, wherein the combination of the swivel bracket and the bracket axle is tiltable about the tilt axle when the tilt axle is inserted in the throughout opening, by:
   connecting the leg gutter to a first axial end of the middle assembly and connecting a second axial end of the middle assembly to the lower assembly to have the middle assembly and the lower assembly extend substantially co-axially, and removably attaching the lower assembly to the base apparatus plate with the use of the tilt axle and the supporting elements;
   positioning the apparatus by placing the base apparatus plate under a patient's leg characterized by a dislocated hip to support the calf of said leg with one of the first and second supporting elongated members in a substantially horizontal orientation; and changing an orientation of the leg secured in the apparatus by at least reorienting a combination of the leg gutter, the middle assembly, and the lower assembly, wherein said reorienting includes (14A) an elevating and lifting combination, and (14B) rotating said combination about the bracket axle and/or tilting said combination about the tilt axle.

3. The method according to claim 2, comprising reversibly applying a lifting traction to the leg by changing a length of the middle assembly.

4. The method according to claim 3, wherein said reversibly applying lifting traction includes placing a femoral head of the leg and a pelvic acetabular fossa in a pre-set position substantially at the same distance from the base apparatus plate.

5. The method according to claim 4, further comprising:
while the femoral head and the pelvic acetabular fossa are maintained in said pre-set position without manual input or effort, repositioning the femoral head into its pelvic acetabular fossa to correct a hip dislocation.

6. A method according to claim 2, wherein said reorienting includes reversibly and/or temporarily immobilizing the lower assembly with respect to a rotational motion about the bracket axle.

7. The method according to claim 6, wherein said immobilizing comprises positioning a free end of the swivel bracket in contact with and/or over the at least one stopper element.

8. The method according to claim 3, further comprising securing the leg in the apparatus by employing first restraining elements to substantially immobilize the calf and the thigh of the leg with respect to the leg gutter and/or employing a second restraining element to limiting a motion of a patient's body with respect to the base apparatus plate.

9. The apparatus according to claim 1, wherein the middle assembly is configured to have the spatial extent thereof changed telescopically.

10. The apparatus according to claim 9, wherein a telescopic mechanical component of the middle assembly is complemented with a bolt affixed thereto and configured to be repositionable along an axis of the telescopic mechanical component.

11. The apparatus according to claim 10, wherein, when the leg gutter includes an internally-threaded cylindrically-shaped tube transversely affixed to one of the first and second supporting elongated members, a thread of the bolt and an internal thread of said cylindrically-shaped tube are mating threads.

12. The apparatus according to claim 1,
wherein the at least one stopper element dimensioned to at least temporarily stop a portion of a body of the apparatus from being rotated about the bracket axle when the lower assembly is attached to the base apparatus plate with the use of the tilt joint and the supporting elements,
wherein the portion of the body is formed by (i) attaching the middle assembly to the lower assembly, and/or by (ii) attaching the middle assembly to the lower assembly and attaching the middle assembly to the leg gutter to form a portion of a body.

13. The apparatus according to claim 12, wherein the tilt joint includes a tilt axle dimensioned to be removably inserted in a throughout opening formed at the end of the bracket axle that is distal to the swivel bracket, wherein the combination of the swivel bracket and the bracket axle is tiltable about the tilt axle when the tilt axle is inserted in the throughout opening.

14. The apparatus according to claim 1,
wherein the swivel bracket includes a top bracket plate and at least one side bracket plate connected to the top bracket plate transversely parallel to the bracket axle,
wherein the at least one side bracket plate extends along the bracket axle, and
wherein the at least one side bracket is dimensioned to interact with the at least one stopper element during a rotation of the swivel bracket about the bracket axle when the lower assembly is attached to the base apparatus plate with the use of the tilt axle and the supporting elements.

15. The apparatus according to claim 14, wherein the tilt joint includes a tilt axle dimensioned to be removably inserted in a throughout opening formed at the end of the bracket axle that is distal to the swivel bracket, wherein the combination of the swivel bracket and the bracket axle is tiltable about the tilt axle when the tilt axle is inserted in the throughout opening.

16. The apparatus according to claim 1,
wherein the lower assembly further comprises a nut on the swivel bracket, and
wherein:
(2A) a first axial end of the middle assembly is configured to be threadingly attachable to a mating thread of the leg gutter section,
and/or
(2B) a second axial end of the middle assembly is configured to be threadingly attachable to the lower assembly via an inner thread of the nut.

17. The apparatus according to claim 1, wherein the tilt joint includes one of:
(3A) a tilt axle dimensioned to be removably inserted in a throughout opening formed at the end of the bracket axle that is distal to the swivel bracket, wherein the combination of the swivel bracket and the bracket axle is tiltable about the tilt axle when the tilt axle is inserted in the throughout opening; and
(3B) a ball-and-socket joint.

18. The apparatus according to claim 1, wherein the first supporting elongated member contains a first open channel and the second supporting elongated member contains a second open channel, said first and second open channels aggregately forming a third open channel of the leg gutter section, the third open channel being spatially bent at said approximately right angle.

19. The apparatus according to claim 1, wherein the middle assembly includes an airjack component and/or a hydraulic jack component and/or a mechanical jack.

20. The apparatus according to claim 1, wherein, when the leg gutter section includes a cylindrically-shaped tube, said cylindrically-shaped tube is internally threaded.

21. A hip relocation apparatus comprising:
a leg gutter section including a first supporting elongated member and a second supporting elongated member, the first and second supporting elongated members connected at respective ends thereof to one another at an approximately right angle;
a middle axially extendable section having an axis and structured to reversibly change a spatial extent thereof along the axis;
a lower structural assembly having a swivel bracket, and a bracket axle, wherein the swivel bracket is rotatable about the bracket axle, and
wherein the bracket axle has an opening extending therethrough transversely to the bracket axle, wherein the bracket axle and a lower end of the middle axially extendable section are configured to be modifiably connectable to one another along the axis with the bracket axle being substantially parallel to the axis, and wherein an upper end of the middle axially extendable section is configured to be disengagingly connected to the leg gutter section to have one of the first and second supporting elongated members be transverse to the axis.

22. The apparatus according to claim 21, wherein the swivel bracket includes a top bracket plate and at least one side bracket plate connected to the top bracket plate transversely parallel to the bracket axle, the bracket axle passing substantially through a center of the top plate with the opening being distal to the top bracket plate.

23. The apparatus according to claim 22, wherein the base apparatus plate further comprises at least one motion restricting element affixed to the surface thereof, and wherein relative spatial coordination of the at least one motion restriction element and the support elements is such that—when
   (24A) the swivel bracket includes a top bracket plate and at least one side bracket plate connected to the top bracket plate transversely parallel to the bracket axle, and
   (24B) the combination of the swivel bracket and the bracket axle of the lower structural assembly is reversibly attached to the base apparatus plate by having the tilt axle pass through the opening and removably secured at the support elements of the base apparatus plate the at least one side bracket plate is reversibly stopped by the at least one motion restricting element during rotation of the swivel bracket about the bracket axle.

24. The apparatus according to claim 23, wherein the swivel bracket and the at least one motion restricting element are configured to ensure that, when the lower structural assembly is reversibly secured to the base apparatus plate via the tilt axle,
   a free end of the at least one side bracket plate, during said rotation of the swivel bracket about the bracket axle, is positioned on top of the at least one motion restricting element and is frictionally restricted from sliding off of or being separated from the at least one motion restricting element unless a rotational force, applied to the swivel bracket, exceeds a force of static friction.

25. The apparatus according to claim 21, further comprising a base apparatus plate carrying support elements secured on a surface thereof, the support elements being configured to removably secure a tilt axle substantially parallel to and separated from the base apparatus plate, wherein a combination of the swivel bracket and the bracket axle of the lower structural assembly is configured to be reversibly tilted about the tilt axle when the tilt axle is passed through the opening and removably secured at the support elements of the base apparatus plate.

* * * * *